United States Patent [19]

Wiedemann et al.

[11] Patent Number: 6,127,581
[45] Date of Patent: Oct. 3, 2000

[54] PROCESS FOR PREPARING FLUORINATED BENZYL ALCOHOLS AND FLUORINATED BENZALDEHYDES

[75] Inventors: Jürgen Wiedemann, Bergheim; Albrecht Marhold, Leverkusen; Claus Dreisbach, Köln, all of Germany

[73] Assignee: Bayer Aktiengesellschaft, Leverkusen, Germany

[21] Appl. No.: 09/369,987

[22] Filed: Aug. 6, 1999

[30] Foreign Application Priority Data

Aug. 13, 1998 [DE] Germany .......................... 198 36 698

[51] Int. Cl.[7] .................................................. C07C 45/63
[52] U.S. Cl. ........................... 568/437; 568/433; 568/814
[58] Field of Search .................... 568/433, 437, 568/814

[56] References Cited

U.S. PATENT DOCUMENTS

| | | | |
|---|---|---|---|
| 3,855,291 | 12/1974 | Archer et al. | 260/562 N |
| 4,167,583 | 9/1979 | Knott et al. | 424/343 |
| 4,845,304 | 7/1989 | Yoshida et al. | 568/433 |
| 5,227,531 | 7/1993 | Metz et al. | 568/433 |

FOREIGN PATENT DOCUMENTS

| | | |
|---|---|---|
| 0265854 | 5/1988 | European Pat. Off. . |
| 0289942 | 11/1988 | European Pat. Off. . |
| 0523668 | 1/1993 | European Pat. Off. . |
| 2333849 | 1/1975 | Germany . |
| 2714042 | 10/1978 | Germany . |
| 3637156 | 5/1988 | Germany . |
| 197 02 282 | 7/1998 | Germany . |
| 197 20 282 | 7/1998 | Germany . |
| 95/19980 | 7/1995 | WIPO . |

OTHER PUBLICATIONS

J. English et al: "The Synthesis of 3,5–difluoro– and 3–fluoro–5–iodo–dl–tyrosine", J. American Chem. Soc., Bd. 62, 1949, Seite 350–353 XP002124525.

Harrison et al, Compendium of Organic Synthetic Methods, pp. 80–84, 1971.

*Primary Examiner*—Sreeni Padmanabhan
*Attorney, Agent, or Firm*—Joseph C. Gil; Diderico van Eyl

[57] ABSTRACT

Fluorinated benzaldehydes are obtainable in a simple and inexpensive manner and in significantly improved yields when chlorinated benzaldehydes are reacted with alkali metal fluorides at temperatures in the range from about 130 to 200° C. in the presence of less than about 2 mol % of quaternary phosphonium salts, based on chlorine atoms to be replaced, at initial concentrations of more than 2.5 mol of the chlorinated benzaldehydes per kg of dipolar aprotic solvent. Fluorinated benzaldehydes obtained in this way can advantageously be hydrogenated with hydrogen in the presence of noble metal catalysts to give fluorinated benzyl alcohols.

17 Claims, No Drawings

PROCESS FOR PREPARING FLUORINATED BENZYL ALCOHOLS AND FLUORINATED BENZALDEHYDES

FIELD OF THE INVENTION

The present invention relates to an improved process for preparing fluorinated benzyl alcohols in high yields and at low cost via the corresponding fluorinated benzaldehydes from the corresponding chlorinated benzaldehydes.

BACKGROUND OF THE INVENTION

Fluorinated benzyl alcohols are not only important intermediates for the preparation of pharmaceuticals and crop protection agents (WO 95/19 980, DE-A 2,714,042) but also have a schistosomacidal action (U.S. Pat. No. 3,855,291) and are used as components in microbicides (DE-A-233, 849, U.S. Pat. No. 4,167,583).

It is known from EP-B 265,854 that fluorobenzaldehydes can be prepared from chlorobenzaldehydes using alkali metal fluorides in a dipolar aprotic solvent. The yield is 68% of theory, which is unsatisfactory.

In addition, the weight ratio of starting material to solvent is 1:5.7, resulting in a poor space-time yield.

EP-B 523,668 describes the preparation of difluorobenzaldehydes from dichlorobenzaldehydes by reaction with alkali metal fluorides in a dipolar aprotic solvent in the presence of ethylene glycol dialkyl ethers as catalyst. The catalyst is used in amounts of from 10 to 50 g per mol of dichlorobenzaldehyde. Even in the unpurified product, the yield of difluorobenzaldehydes is always less than 75%. The solvent is used in an amount of 400 g per mol of dichlorobenzaldehyde, which corresponds to 2.5 mol of dichlorobenzaldehyde per kg of solvent. A disadvantage is the large amounts of catalyst and solvent which are employed to achieve only an unsatisfactory yield.

According to EP-B 289,942, fluorobenzaldehydes are prepared by reacting chlorobenzaldehydes with metal fluorides in bulk or in aromatic hydrocarbons in the presence of quaternary phosphonium salts and/or quaternary ammonium salts and, if desired, further catalysts. The catalysts are used in amounts of from 5 to 50 mol %, based on the chlorobenzaldehyde. The yields are in the range from 41 to 75% but only reach values above 55% when a mixture of two different types of catalyst is used. Even then, the yields are still unsatisfactory.

The previously described processes of the prior art for preparing fluorinated benzaldehydes all require high temperatures and give products containing by-products which can be removed only with great difficulty. Both are disadvantages, high temperatures because they require a lot of energy and by-products which are difficult to remove because they cannot be tolerated in intermediates for active compounds. If the temperature is lowered, e.g., in the process of DE-A 3,637,156, the yield also drops drastically even when longer reaction times are employed (see Comparative Example).

It is also known that fluorinated benzyl alcohols can be obtained from the corresponding benzoic acids by reduction with lithium aluminum hydride or from the corresponding benzoyl chlorides by reduction with alkali metal boranates. The starting materials used here are fluorine-substituted acid chlorides in which the fluorine has been introduced via a halogen replacement reaction or aminobenzoic acids which have been converted into fluorine-substituted derivatives by diazotization in hydrogen fluoride or by the method of Balz-Schiemann (see Houben-Weyl, Methoden der organischen Chemie, 4th edition, volume 5/3, pages 215 and 227). All these processes require the use of metal hydride reagents in the reduction to the benzyl alcohol and therefore can be carried out in industry only with difficulty. In addition, they are expensive.

A further source of fluorinated benzyl alcohols is the corresponding benzyl chlorides or bromides which can be obtained by side-chain halogenation of the corresponding fluorinated toluenes. However, these toluenes are frequently difficult to obtain or can only be prepared from the products which are of interest here.

DE-A 2,333,849 discloses that 2,4-difluorobenzaldehyde can be converted into 2,4-difluorobenzyl alcohol in a yield of 68.6% by hydrogenation over Raney nickel. Disadvantages of this process are not only the large amount of catalyst (31 g per mol) and the large amount of a solvent (1100 ml per mole) but also the unsatisfactory yield of 68.6%. These factors result in an unsatisfactory space-time yield. The aldehyde used was obtained here from the difficult-to-obtain 2,4-difluorotoluene by side-chain chlorination and subsequent hydrolysis.

In summary, it can be said of the prior art that there has hitherto been no satisfactory process for preparing fluorinated benzaldehydes from chlorinated benzaldehydes, since this reaction has hitherto been able to be carried out only at unsatisfactory yields and does not give the desired products in the required purity, even when it is carried out in dilute medium or using two catalysts, and that the preparation of fluorinated benzyl alcohols by reduction has hitherto either required difficult-to-handle and expensive reducing agents or has started from difficult-to-obtain starting materials or, in the case of the reduction of corresponding aldehydes with hydrogen in the presence of Raney nickel, has given only moderate yields. The yields and purities of the products obtainable by the known methods do not satisfy, in particular, the requirements for the synthesis of active compounds.

DESCRIPTION OF THE INVENTION

A process has now been found for preparing fluorinated benzyl alcohols of the formula (I)

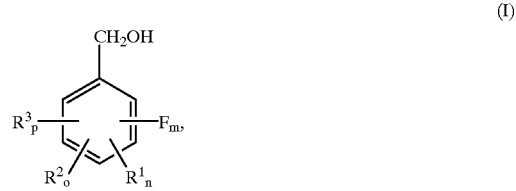

where

R$^1$ represents C$_1$–C$_4$-fluoroalkyl,

R$^2$ represents chlorine,

R$^3$ represents C$_1$–C$_8$-alkyl, m represents an integer from 1 to 4 and n, o and p each represent, independently of one another, zero or an integer from 1 to 3, where: m+n+o+p≦5, which is characterized in that chlorinated benzaldehydes of the formula (II)

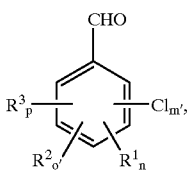

(II)

where
R¹, R², R³, n and p are as defined for formula (I) and
m' represents zero or an integer from 1 to 3 and
o' represents an integer from 1 to 3,
where: m'+n+o'+p≦5,
are reacted with alkali metal fluorides at temperatures in the range from 130 to 200° C. in the presence of less than 2 mol % of quaternary phosphonium salts (based on chlorine atoms to be replaced) at initial concentrations of more than 2.5 mol of the chlorinated benzaldehyde of the formula (II) per kg of dipolar aprotic solvent to give fluorinated benzaldehydes of the formula (III)

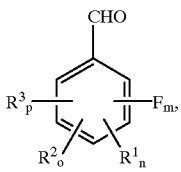

(III)

where the symbols used are as defined for formula (I), and these are hydrogenated with hydrogen in the presence of noble metal catalysts.

A process has also been found for preparing fluorinated benzaldehydes of the formula (III) which is characterized in that chlorinated benzaldehydes of the formula (II) are reacted with alkali metal fluorides at temperatures in the range from 130 to 200° C. in the presence of less than 2 mol % of quaternary phosphonium salts (based on chlorine atoms to be replaced) at initial concentrations of more than 2.5 mol of the chlorinated benzaldehyde of the formula (II) per kg of dipolar aprotic solvent.

The symbols used in the formulae (I) to (III) preferably have the following meanings:
R¹=trifluoromethyl or pentafluoroethyl,
R²=chlorine,
R³=$C_1$–$C_4$-alkyl, in particular, methyl or ethyl,
m=an integer from 1 to 3, in particular, 1 or 2,
n, o and p, independently of one another=zero or 1,
where m+n+o+p<3,
m'=zero, 1 or 2 and
o'=1 or 2,
where m'+n+o'+p≦3.

Particularly preferably, 2,6-dichlorobenzaldehyde is used in the process of the invention and 2-fluoro-6-chlorobenzaldehyde, 2-fluoro-6-chlorobenzyl alcohol, 2,6-difluorobenzaldehyde or 2,6-difluorobenzyl alcohol is obtained or 2,4-dichlorobenzaldehyde is used and 2,4-difluoro-benzaldehyde or 2,4-difluorobenzyl alcohol is obtained or 3,4-dichloro-benzaldehyde is used and 3-chloro-4-fluorobenzaldehyde or 3-chloro-4-fluorobenzyl alcohol is obtained.

The chlorinated benzaldehydes of the formula (II) required as starting material can be obtained simply and inexpensively from the corresponding toluenes by ring and side-chain chlorination and subsequent hydrolysis.

Suitable alkali metal fluorides are, for example, sodium, potassium, rubidium and caesium fluoride or mixtures thereof. It is advantageous to dry the alkali metal fluorides used prior to the reaction, e.g., by spray-drying them or heating the alkali metal fluoride with solvents and thus distilling off a mixture of water and solvent. Preference is given to using potassium fluoride, if desired, in admixture with caesium fluoride. Alkali metal fluorides can be used, for example, in amounts of from 0.8 to 2 mol per mol of chlorine atoms to be replaced. This amount is preferably from 1.1 to 1.6 mol.

The following further measures are, independently of one another, preferred in the fluorination according to the invention:
the presence of less than 1.8 mol % of quaternary phosphonium salts (based on chlorine atoms to be replaced);
the use of tetraorganophosphonium halides, in particular, tetraphenylphosphonium bromide, as quaternary phosphonium salt;
an initial concentration of more than 2.8 mol of the chlorinated aldehyde of the formula (II) per kg of dipolar aprotic solvent;
the use of diphenyl sulphone, tetramethylene sulphone, dimethyl sulphoxide, tetramethylene sulphoxide, dimethylacetamide, dimethylformamide, N-methylpyrrolidone or any mixtures thereof, in particular of tetramethylene sulphone, as dipolar aprotic solvent;
reaction temperatures in the range from 150 to 200° C.;
the use of chlorinated aldehydes of the formula (II) whose water content is as low as possible and dipolar aprotic solvents whose water content is as low as possible,
carrying out the reaction and handling the chlorinated and fluorinated benzaldehydes under a protective gas atmosphere.

After the fluorination reaction is complete, the fluorinated benzaldehyde of the formula (III), which has been prepared can be separated from the reaction mixture, for example, by distilling it out under reduced pressure. If desired, it can be purified further, e.g., by fractional distillation under reduced pressure. The fluorinated benzaldehydes of the formula (III) are generally obtained as isolated product in yields of over 75%.

It is advantageous for the fluorinated benzaldehyde of the formula (III) being formed to be continuously distilled from the reaction mixture and/or for the starting material to be fed continuously to the reaction mixture.

Preferred catalysts for the catalytic hydrogenation according to the invention are palladium, platinum and ruthenium catalysts, in particular palladium catalysts.

The noble metal is preferably applied to a support material. Examples of suitable support materials are silicas, aluminum oxides, silicates, carbonates, sulphates or carbons of many different types. Preferred support materials are carbons. Particularly preferred noble metal catalysts are palladium-on-carbon catalysts. The supported catalysts can contain, for example, from 0.1 to 20% by weight of noble metal, based on the weight of the support material. This amount is preferably from 0.5 to 15% by weight, in particular, from 1 to 10% by weight. Suitable noble metal catalysts, in particular those containing palladium-on-carbon, are commercially available.

The noble metal catalysts, in particular, supported noble metal catalysts (in that case taking into account only the noble metal present), can be used, for example, in amounts of from 0.00001 to 5% by weight, based on the fluorinated aldehyde of the formula (III). This amount is preferably from 0.0001 to 2% by weight.

The catalytic hydrogenation according to the invention can be carried out in the presence or absence of solvent. Suitable solvents are, for example, aliphatic and aromatic hydrocarbons, ethers, esters and alcohols which are liquid under the reaction conditions, in particular, $C_5$–$C_{12}$-aliphatics, $C_6$–$C_{10}$-aromatics, $C_7$–$C_{10}$-alkylaromatics, di-$C_2$–$C_5$-alkyl ethers (including asymmetric ethers), cyclic ethers, esters having a total of from 3 to 15 carbon atoms and alcohols having from 1 to 12 carbon atoms. The reaction can be carried out in the absence of a solvent if the fluorinated aldehyde of the formula (III) which is used is liquid under the reaction conditions. The reaction is preferably carried out in the presence of $C_1$–$C_4$-alkyl alcohols or toluene or without addition of solvent.

If solvents are used, the amount of a solvent is not critical, for example, it is possible to use from 0 to 1500% by weight of solvent, based on fluorinated benzaldehyde of the formula (III).

The hydrogenation according to the invention can be carried out, for example, at temperatures in the range from −30 to +300° C. The temperature is preferably in the range from 0 to 150° C., in particular, in the range from 20 to 100° C.

The hydrogenation according to the invention can be carried out, for example, at pressures in the range from 1 to 300 bar. The pressure is preferably in the range from 2 to 150 bar, in particular, in the range from 5 to 100 bar.

The reaction mixture present, after the hydrogenation is complete, can be worked up, for example, by separating off the solid constituents, e.g., by filtration, and distilling any solvent present from the filtrate. After carrying out the hydrogenation, the fluorinated benzyl alcohols of the formula (I) are generally obtained in yields of 80% and above, frequently 90% and above.

The catalytic hydrogenation can be carried out, for example, as a liquid-phase, trickling-phase or gas-phase hydrogenation over fixed-bed noble metal catalysts.

The processes of the invention allow the preparation of fluorinated benzaldehydes and benzyl alcohols in yields which are significantly higher than in the prior art. In addition, products which are purer than hitherto are obtained.

In addition, the fluorination requires only one type of catalyst in a small amount, and it can be carried out in concentrated solution. In the hydrogenation, difficult-to-handle and expensive reducing agents are avoided and, despite this, yields which are more than 10% higher are achieved.

The invention is further illustrated in the following examples in which all parts and percentages are by weight unless otherwise indicated.

EXAMPLES

Example 1

Under nitrogen, a suspension of 348 g of potassium fluoride in 700 ml of tetramethylene sulphone was stirred at 100° C. for 1.5 hours. Subsequently, 200 ml of the liquid volume were distilled off. 350 g of 2,6-dichlorobenzaldehyde were then added in a countercurrent of nitrogen. After addition of 20.4 g of tetraphenylphosphonium bromide, the reaction mixture was heated at 170° C. for 15 hours while stirring under nitrogen. The course of the reaction was followed by gas chromatography. After the reaction was complete, 2,6-difluorobenzaldehyde was distilled from the reaction mixture (boiling range up to 145° C. at 18 mbar) and was subsequently freed of impurities by fractional distillation. The boiling point of the 2,6-difluorobenzaldehyde was from 68 to 70° C. at 11 mbar. The yield was 80% of theory and the purity of the product was over 98% (GC).

Example 2

Under nitrogen, a suspension of 348 g of potassium fluoride in 700 ml of tetramethylene sulphone was stirred at 100° C. for 1.5 hours. Subsequently, 200 ml of the liquid volume were distilled off. 350 g of 2,4-dichlorobenzaldehyde were then added in a countercurrent of nitrogen. After addition of 30 g of tetraphenylphosphonium bromide, the reaction mixture was heated at 160° C. for 16 hours while stirring under nitrogen. The course of the reaction was followed by gas chromatography. After the reaction was complete, 2,4-difluorobenzaldehyde was distilled from the reaction mixture (boiling range up to 145° C. at 18 mbar) and was subsequently freed of impurities by fractional distillation. The boiling point of the 2,4-difluorobenzaldehyde was 48° C. at 11 mbar. The yield was 79% of theory and the purity was over 98% (GC).

Examples 3 to 8

The 2,6-difluorobenzaldehyde used in each case had been obtained as described in Example 1.

Example 3

332 g of 2,6-difluorobenzaldehyde were placed under nitrogen in a 0.7 l autoclave and admixed with 6.4 g of 5% strength by weight palladium-on-carbon (catalyst from Heraeus type K-0227, containing 50% by weight of water). The autoclave was closed and purged with nitrogen. 50 bar of hydrogen were then injected and the contents of the autoclave were heated to 80° C. Hydrogenation was carried out for a total of 4 hours while stirring. After cooling and venting, the reaction mixture was filtered through Celite® filter aid, the autoclave was rinsed with 50 g of isopropanol and the filter cake was washed with 150 g of isopropanol. The solvent was distilled from the combined filtrates and washings and the crude product mixture was subsequently distilled off. 288 g of 2,6-difluorobenzyl alcohol were obtained (90% of theory).

Example 4

5 g of 2,6-difluorobenzaldehyde were dissolved in 100 ml of isopropanol, admixed with 1 g of the catalyst also used in Example 3 and the mixture was transferred to an autoclave. 50 bar of hydrogen were then injected and the contents of the autoclave were heated to 50° C. Hydrogenation was carried out for a total of 5 hours while stirring. The reaction mixture was then filtered and isopropanol was distilled from the filtrate. The crude yield of 2,6-difluorobenzyl alcohol was 94% of theory.

Example 5

5 g of 2,6-difluorobenzaldehyde were dissolved in 100 ml of isopropanol, admixed with 0.075 g of the catalyst also used in Example 3 and transferred to an autoclave. 50 bar of hydrogen were then injected and the contents of the autoclave were heated to 80° C. Hydrogenation was carried out for a total of 5 hours while stirring. The reaction mixture was then filtered and isopropanol was distilled from the filtrate. The crude yield of 2,6-difluorobenzyl alcohol was 95% of theory.

Example 6

7.5 g of 2,6-difluorobenzaldehyde were dissolved in 100 ml of isopropanol, admixed with 1.25 g of 1% by weight platinum-on-carbon (wet, 50% by weight of water) as catalyst and the mixture was transferred to an autoclave. 50 bar of hydrogen were then injected and the contents of the autoclave were heated to 50° C. Hydrogenation was carried out for a total of 10 hours while stirring. The reaction mixture was then filtered and isopropanol was distilled from the filtrate. The crude yield of 2,6-difluorobenzyl alcohol was 92% of theory.

Example 7

7.5 g of 2,6-difluorobenzaldehyde were dissolved in 100 ml of isopropanol, admixed with 1.25 g of the catalyst also used in Example 6 and the mixture was transferred to an autoclave. 50 bar of hydrogen were then injected and the contents of the autoclave were heated to 80° C. Hydrogenation was carried out for a total of 10 hours while stirring. The reaction mixture was then filtered and isopropanol was distilled from the filtrate. The crude yield of 2,6-difluorobenzyl alcohol was 84% of theory.

Example 8

5 g of 2,6-difluorobenzaldehyde were dissolved in 100 ml of isopropanol, admixed with 1.5 g 5% weight ruthenium-on-carbon (wet, 50% by weight of water) as catalyst and the mixture was introduced into an autoclave. 50 bar of hydrogen were then injected and the contents of the autoclave were heated to 50° C. Hydrogenation was carried out for a total of 5 hours while stirring. The reaction mixture was then filtered and isopropanol was distilled from the filtrate. The crude yield of 2,6-difluorobenzyl alcohol was 80% of theory.

Example 9

2.5 g of 2,4-difluorobenzaldehyde (obtained as described in Example 2) were dissolved in 20 ml of toluene, admixed with 0.2 g of the catalyst also used in Example 3 and the mixture was introduced into an autoclave. 50 bar of hydrogen were then injected and the contents of the autoclave were heated at 80° C. for 10 hours. The reaction mixture was then filtered and toluene was distilled from the filtrate. The yield of 2,4-difluorobenzyl alcohol was 98% of theory.

Example 10 (Comparative Example to DE-A 3,637,156)

a) Under nitrogen, a suspension of 348 g of potassium fluoride in 700 ml of tetramethylene sulphone was stirred at 100° C. for 1.5 hours. 200 ml of the liquid volume were subsequently distilled off. 350 g of 2,6-dichlorobenzaldehyde were then added in a countercurrent of nitrogen. The reaction mixture was heated at 170° C. for 33 hours while stirring under nitrogen. After the reaction was complete, the products were distilled from the reaction mixture (boiling range: up to 145° C. at 18 mbar) and subsequently freed of solvent and impurities by fractional distillation (b.p.11: 68–70° C.).

Yield: 65 g=23% of theory of. 2-chloro-6-fluorobenzaldehyde only traces of 2,6-difluorobenzaldehyde b) Experiment a) was repeated at a reaction temperature of 220° C. and a reaction time of 20 hours. This gave 2,6-difluorobenzaldehyde in a yield of 44% of theory together with 22% of theory of 2-chloro-6-fluorobenzaldehyde. Only traces of the starting material could be detected.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing fluorinated benzyl alcohols of the formula (I)

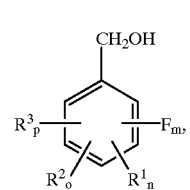

(I)

wherein $R^1$ is a component selected from the group consisting of $C_1$–$C_4$-fluoroalkyl groups, $R^2$ is chlorine, $R^3$ is a component selected from the group consisting of $C_1$–$C_8$-alkyl groups, m is an integer from 1 to 4 and n, o and p each represent, independently of one another, zero or an integer from 1 to 3, where: $m+n+o+p \leq 5$, and wherein A) chlorinated benzaldehydes of the formula (II)

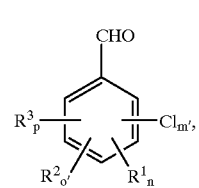

(II)

wherein $R^1$, $R^2$, $R^3$, n and p are as defined for formula (I) and m' is zero or an integer from 1 to 3 and o' is an integer from 1 to 3, where: $m'+n+o'+p \leq 5$, are reacted with B) alkali metal fluorides at a temperature in the range of from about 130 to 200° C. in the presence of quaternary phosphonium salts in a catalytically effective amount that is less than about 2 mol %, based on chlorine atoms to be replaced, at initial concentrations of more than 2.5 mol of the chlorinated benzaldehyde of the formula (II) per kg of dipolar aprotic solvent to give fluorinated benzaldehydes of the formula (III)

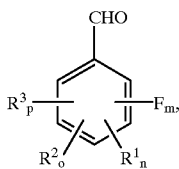

wherein the symbols $R^1$, $R^2$, and $R^3$ used are as defined for formula (I), and these benzaldehydes of the formula (III) are hydrogenated with hydrogen in the presence of noble metal catalysts.

2. Process for preparing fluorinated benzaldehydes of the formula (III)

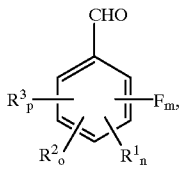

wherein
- $R^1$ is a component selected from the group consisting of $C_1$–$C_4$-fluoroalkyl groups,
- $R^2$ is chlorine,
- $R^3$ is a component selected from the group consisting of $C_1$–$C_8$-alkyl groups,
- m is an integer from 1 to 4 and
- n, o and p each is, independently of one another, zero or an integer from 1 to 3,
  where: $m+n+o+p \leq 5$,
  wherein
  A) chlorinated benzaldehydes of the formula (II)

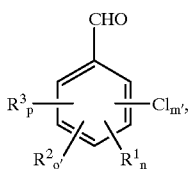

wherein
- $R^1$, $R^2$, $R^3$, n and p are as defined for formula (I) and
- m' is zero or an integer from 1 to 3 and
- o' is an integer from 1 to 3,
  where: $m'+n+o'+p \leq 5$,
  are reacted with
  B) alkali metal fluorides at temperatures in the range of from about 130 to 200° C. in the presence of quaternary phosphonium salts in a catalytically effective amount that is less than about 2 mol %, based on chlorine atoms to be replaced, at initial concentrations of more than about 2.5 mol of the chlorinated benzaldehyde of the formula (II) per kg of dipolar aprotic solvent.

3. Process according to claim 1, wherein the symbols used in the formulae (I) to (III) have the following meanings:
- $R^1$ is trifluoromethyl or pentafluoroethyl,
- $R^2$ is chlorine,
- $R^3$ is a component selected from the group consisting of $C_1$–$C_4$-alkyl groups,
- m is an integer from 1 to 3,
- n, o and p, independently of one another is zero or 1, where
  $m+n+o+p \leq 3$,
- m' is zero, 1 or 2 and
- o' is 1 or 2, where $m'+n+o'+p \leq 3$.

4. Process according to claim 1, wherein 2,6-dichlorobenzaldehyde is used and a component comprising a member selected from the group consisting of 2-fluoro-6-chlorobenzaldehyde, 2-fluoro-6-chlorobenzyl alcohols, 2,6-difluorobenzaldehyde and 2,6-difluorobenzyl alcohols is obtained.

5. Process according to claim 1, wherein 2,4-dichlorobenzaldehyde is used and a component comprising a member selected from the group consisting of 2,4-difluorobenzaldehyde and 2,4-difluorobenzyl alcohol is obtained.

6. Process according to claim 1, wherein 3,4-dichlorobenzaldehyde is used and a component comprising a member selected from the group consisting of 3-chloro-4-fluorobenzaldehyde and 3-chloro-4-fluorobenzyl alcohol is obtained.

7. Process according to claim 1, wherein the alkali metal fluoride is potassium fluoride.

8. Process of claim 7, wherein the potassium fluoride is used in an admixture with caesium fluoride.

9. Process according to claim 1, wherein the process is carried out in the presence of less than about 1.8 mol % of quaternary phosphonium salts, based on chlorine atoms to be replaced, the process is commenced at an initial concentration of more than about 2.8 mol of the chlorinated aldehyde of the formula (II) per kg of dipolar aprotic solvent, tetramethylene sulphone is used as dipolar aprotic solvent, a reaction temperature ranging from about 150 to 200° C. is maintained and the reaction procedure and the handling of the chlorinated and fluorinated benzaldehydes are carried out under a protective gas atmosphere.

10. Process according to claim 1, wherein the catalytic hydrogenation is carried out using a component selected from the group consisting of palladium, platinum and ruthenium catalysts, and wherein the component is applied to a support material.

11. Process according to claim 10, wherein the supported catalysts contain from 0.1 to 20% by weight of noble metal, based on the support material.

12. Process according to claim 1, wherein the catalytic hydrogenation is carried out in the presence of a component selected from the group consisting of aliphatic or aromatic hydrocarbons, ethers, esters and alcohols which are liquid under the reaction conditions.

13. Process according to claim 1, wherein the fluorinated benzaldehyde of the formula (III) that forms is continuously distilled from the reaction mixture.

14. Process according to claim 1, wherein the starting material is continuously fed to the reaction mixture.

15. The process of claim 1, wherein the fluorinated benzyl alcohols of the formula (I) are obtained at a yield that is at least about 80%.

16. The process of claim 1, wherein the fluorinated benzyl alcohols of the formula (I) are obtained at a yield that is at least about 90%.

17. The process of claim 2, wherein the fluorinated benzaldehydes of the formula (III) are obtained at a yield that is greater than about 75%.

* * * * *